US006190366B1

(12) United States Patent
Tani

(10) Patent No.: US 6,190,366 B1
(45) Date of Patent: Feb. 20, 2001

(54) PORTABLE, LOCALLY WASHING HYGIENIC DEVICE

(76) Inventor: Kanari Tani, 70, Minamigaoka 4-chome, Ohnojo-shi, Fukuoka (JP)

( * ) Notice: Under 35 U.S.C. 154(b), the term of this patent shall be extended for 0 days.

(21) Appl. No.: 09/386,022

(22) Filed: Aug. 30, 1999

(30) Foreign Application Priority Data

Aug. 31, 1998 (JP) .................................................. 10-245183
Aug. 11, 1999 (JP) .................................................. 11-227834

(51) Int. Cl.[7] ......................... A61M 31/00; A61M 5/178; A61M 5/00; B65D 37/00; B05B 11/06

(52) U.S. Cl. ............................ 604/279; 604/37; 604/262; 222/92; 222/211; 222/633

(58) Field of Search .................................. 604/36, 37, 39, 604/246, 257, 262, 275, 279, 185, 514, 515, 75; 222/148, 149, 151, 211, 566–568, 630–633, 92, 95

(56) References Cited

U.S. PATENT DOCUMENTS 3,626,939 * 12/1971 Maltenfort et al. .................. 604/275
3,993,070 * 11/1976 Sneider ................................ 604/262
4,636,412 * 1/1987 Field .................................... 604/262
4,772,274 * 9/1988 Lukacs ................................. 604/275
4,776,848 * 10/1988 Solazzo ................................ 604/247
4,964,852 * 10/1990 Dunning et al. ....................... 604/75
4,991,777 * 2/1991 Sato ..................................... 604/275

* cited by examiner

*Primary Examiner*—Richard K. Seidel
*Assistant Examiner*—Michael Hayes
(74) *Attorney, Agent, or Firm*—Jordan and Hamburg LLP

(57) ABSTRACT

The portable, locally washing hygienic device has a water container of a flexible synthetic resin film member, a water supply tube mounted on the water container and acting as a water passage, a spray nozzle mounted on an upper portion of the water supply tube, and a valve assembly interposed between the spray nozzle and the water supply tube, in which a lower portion of the water supply tube located within the water container is joined together through a connecting member with an inner surface portion of the water container by thermally fusing or otherwise.

15 Claims, 8 Drawing Sheets

PORTABLE, LOCALLY WASHING HYGIENIC DEVICE

BACKGROUND OF THE INVENTION

1. Field of the Invention

The present invention relates to a portable, locally washing hygienic device and, more particularly, to a portable, locally washing hygienic device which is so adapted as to be portable enough to allow a person to carry and to wash a part of the body, particularly anus or vagina, with water and clean it in a toilet where no locally washing device is installed.

2. Description of the Related Art

Japanese Patent Publication Nos. 9-84,715 and 9-327,495 disclose each a portable, locally washing hygienic device which comprises a motor, a battery or an electric cell for driving the motor, a water container for accommodating water, and a water-jet nozzle system for jetting water to such a part of the body.

Upon use of such a portable, locally washing hygienic device, the water container is filled with water prior to use and then a switch is pressed to start driving the motor to allow the water-jet nozzle system to jet streams of water onto or into the part of the body, thereby locally washing the part of the body with water streams jetted from the nozzle system.

Further, Japanese Patent Publication Nos. 9-28,611 and 9-238,865 disclose each a portable, locally washing hygienic device for washing the part of the body with water by jetting streams of water from a water-jet nozzle system of a flexible water container and pressing the water container to allow the water to jet therefrom for washing the part of the body.

The prior art portable, locally washing hygienic devices which are each provided with the motor, battery and water container tend to become heavy in weight due to the weight of each part and large in size because they require each a space in which to install those parts therein. Therefore, those prior art devices are too heavy and less compact in carrying them personally.

On the other hand, the prior art portable, locally washing hygienic devices with the water container made of a flexible material can be made lightweight, however, the size of the water container is too large to be compact enough to allow the user to readily carry them personally.

Therefore, big demands have been created to develop a portable, locally washing hygienic device that can overcome the drawbacks and shortcomings of the prior art portable, locally washing hygienic devices and that is sufficiently compact in allowing the user to carry it personally with ease. Further, it is required to be disposed of readily if it would become useless or it would be no longer used.

DISCLOSURE OF THE INVENTION

The present invention has the object to provide a portable, locally washing hygienic device that is lightweight and compact in size and has an improved feature of carrying it personally with ease. Moreover, the portable, locally washing hygienic device according to the present invention is disposable so that it can be disposed of readily when it becomes no longer needed.

In order to achieve the object as described above, the present invention in accordance with an embodiment provides a portable, locally washing hygienic device which comprises a water container made of flexible sheets produced by subjecting a synthetic plastic film member to thermal fusion or otherwise to form a flexible bag; a water supply tube mounted on the flexible water container and acting as a water passage for supplying water from the water container; a spray nozzle for spraying the water onto the target part of an object, mounted on an edge portion of the water supply tube; and a valve assembly interposed between a bottom end portion of the spray nozzle and a top end portion of the water supply tube; wherein a portion of the water supply tube located within the water container is joined securely or integrally together with an inner surface portion of the water container by thermally fusing or otherwise. This feature of the portable, locally washing hygienic device according to the present invention can be made lightweight and compact in size to be carried with ease because the portion of the water container can be folded and accommodated, for example, in a small and compact bag or the like.

In a preferred mode of the embodiment according to the present invention, the water supply tube is provided with a connecting member such as, e.g., a plate-shaped connection which in turn can be connected and firmly fixed with the inner surface portion of the water container by thermally fusing or otherwise. With this configuration, the spray nozzle does not displace the position of the spray nozzle to an extent to which the user should otherwise pay attention, whenever the user grips and press the water container for use in washing, and thereby the portable hygienic device of this invention can ensure a substantially constant direction of spraying the water therefrom onto the target part of the object. Therefore, the portable hygienic device of the present invention can present the advantage in that the water can be always sprayed in a desired and constant direction without causing the spray nozzle to vary its spraying position during use. On the other hand, if the water supply tube would not be attached to the inner surface portion of the water container, like such prior art portable hygienic devices, the spray nozzle mounted on the water supply tube may be caused to vary the direction of spraying the water from the nozzle head onto the target part of the object to a great extent to which the user should make sure to which position the spray nozzle is directed, whenever the water container is gripped and pressed by the hand of the user and the water is forced out from the water container into the spray nozzle for washing the target site of the object. This is very inconvenient for the user because the user should take care of the direction of spraying the water from the spray nozzle, whenever the user grips and presses the water container to wash the target site of the object with the water sprayed through the spray nozzle.

In another preferred mode of the embodiment according to the present invention, the valve assembly may comprise a casing with a water passage hole or holes, a valve section made of an elastic material, and a pressing member for pressing the valve section toward the casing and fixing it thereto in such a manner that the water passage hole and holes can be closed by the valve section. In this configuration, a pressure can be applied to the water present in the water container by gripping and pressing the water container with the hands by force, so that the valve section is caused to be transformed by the pressure applied thereto, thereby to jet the water from the water container through the water supply tube to the spray nozzle. On the other hand, when no pressure is applied to the water container, no water is forced to flow through the water supply tube from the water container, so that the one-way valve section of the valve assembly is caused to automatically close the water passage of the water supply tube. This leads to automatically closing the water passage toward the spray nozzle from the water supply tube, on the one hand, and preventing the water remaining in the water passage of the spray nozzle from returning to the water container, on the other hand. This can keep the water present in the water container in a clean state and maintain a clean sanitation for reuse of the water container. In particular, the valve section acting as a movable section is made of no metal so that it can be disposed of with ease because it does not require any laborious work for removing such metal parts from hygienic devices to be disposed of.

In a further preferred mode of the embodiment according to the present invention, the water supply tube may include a curved section at its upper portion in such a manner that the water supply tube is connected to the spray nozzle in a curved fashion. Therefore, the user can use this device in a natural posture, i.e., the user can wash the local part of the body without assuming an artificial or unnatural posture so as to adapt to the direction of spraying the water therefrom.

In a still further preferred mode of the embodiment according to the present invention, a nozzle head is detachably disposed on the top end portion of the spray nozzle. The nozzle head may be provided with a plurality of a spraying hole or holes disposed at different positions. Therefore, the portable, locally washing hygienic device according to the present invention can assume a different state of spraying the water so as to comply with versatile uses of the portable hygienic device simply by exchanging the nozzle heads so as to adapt to such an intended use.

In particular, in a still further preferred mode of the embodiment according to the present invention, the nozzle head is disposed at the top end of the spray nozzle so as to rotate about the spray nozzle, so that the direction of, spraying the water can be adjusted in an accurate way.

In still further preferred modes of the embodiment of the present invention, the firmly fixed (thermally fused, etc.) portion of the water container is fringed at its outer peripheral edge with a continuous series of wave-shaped cuts or otherwise or the outer peripheral edge portion of the water container is thermally fused into a bag with a portion left non-fixed and the outer peripheral non-fixed portion of the water container is fringed with a continuous series of wave-shaped cuts or otherwise. This configuration can prevent the hand of the user from being wounded by the otherwise sharp side edge of the water container.

Other objects, features and advantages of the present invention will become apparent in the course of the description with reference to the accompanying drawings.

BRIEF DESCRIPTION OF THE ACCOMPANYING DRAWINGS

DESCRIPTION OF THE PREFERRED EMBODIMENTS

Figure 1:
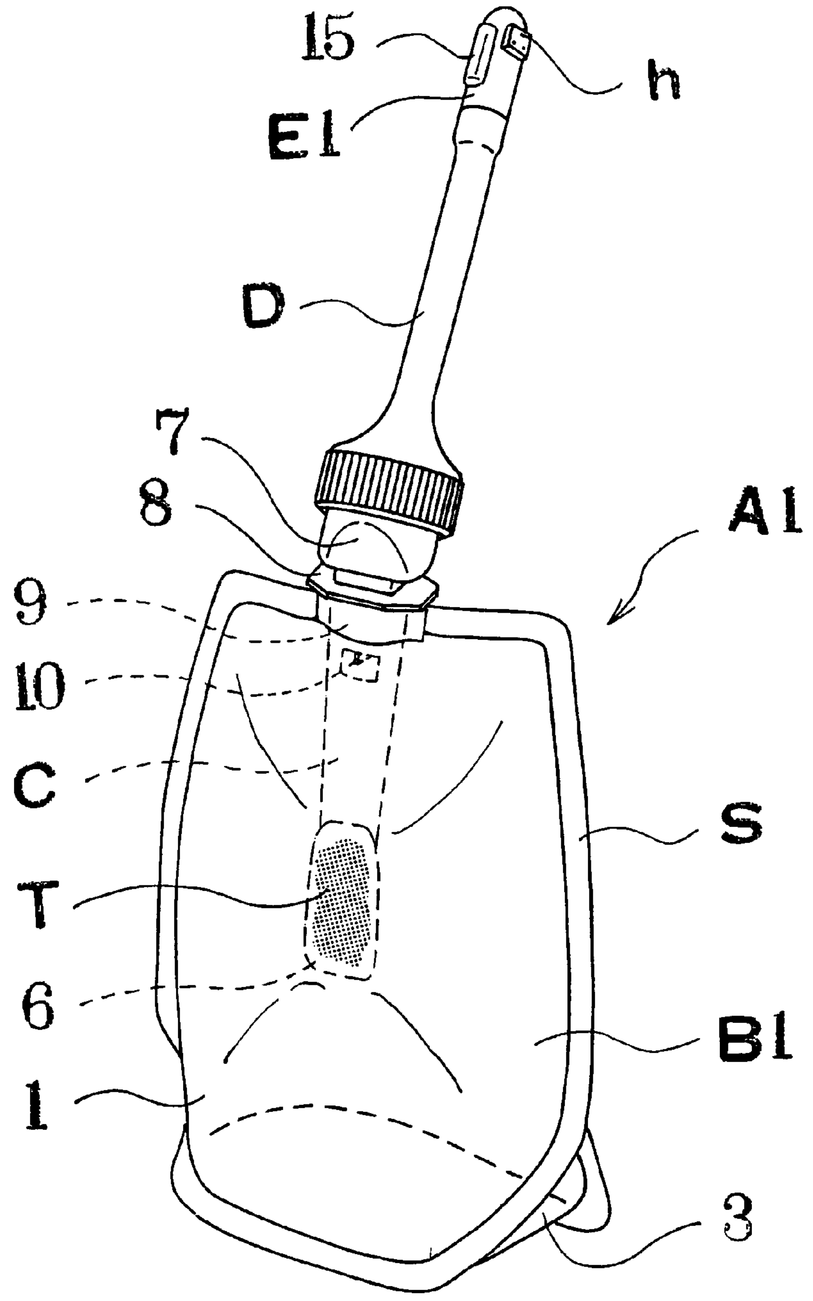
FIG. 1 is a perspective view showing a portable, locally washing hygienic device according to a first embodiment of the present invention.

The portable, locally washing hygienic device according to the present invention, which may comprise a water container for accommodating water, a water supply tube mounted on the water container and acting as a water passage from the water container for washing, a spray nozzle mounted on the water supply tube, a nozzle head mounted on a top portion of the spray nozzle and a valve assembly interposed between the water supply tube and the spray nozzle. The portable, locally washing hygienic device according to the present invention is characterized in that a portion of the water supply tube located within the water container is integrally formed with the inner surface portion of the water container.

The water container for the portable hygienic device may be prepared by a synthetic resin film member formed in such a manner that a synthetic resin film acting as the innermost surface portion of the synthetic resin film member may be made of a thermally fusable polyethylene or polypropylene type resin and an appropriate synthetic resin film or another material such as, for example, paper, an aluminum foil, etc. is laminated on the resin film. The material for the water container is not limited to those materials as described above and any other material can be used as long as it can appropriately be used for the resulting bag-shaped water container.

The resulting film member is then formed in conventional manner into a bag-shaped container in which water can be accommodated, for example, by thermally fusing the film member with each other so as to locate the resin film at the innermost surface portion of the water container. Although the water container may assume any appropriate shape as long as it can accommodate water therein and it can be used as a portable, locally washing hygienic device, the water container for use as the portable hygienic device may comprise a front wall section, a rear wall section, and a bottom section or a side wall section, each being made of the such synthetic plastic film member, and each being joined securely together with one another by thermally fusing or otherwise to form a bag-shaped container. More specifically, the water container in an embodiment of the present invention may be formed such that the front wall section and the rear wall section are joined securely together at their top and side portions with each other and the bottom section is joined securely together with the bottom portions of the front and rear wall sections, in each case, by thermally fusing or otherwise, to form a bag-shaped container. Alternatively, the water container in a second embodiment may be configured such that the front wall section and the rear wall section are likewise joined securely together at the upper and bottom end portions and that each side portion of the front and rear wall sections are joined together with the respective side portion of the side sections by thermally fusing or otherwise. With this configuration of the water container, when the water container is filled with water to its full extent and it is extended outwardly by the water filled therein, the water container in the first embodiment may be shaped in a generally oval form, when viewed from bottom, and in a generally triangular form, when viewed from the side. Likewise, the water container in the second embodiment may be shaped in a generally oval form, when viewed from the side. Therefore, the water container is filled with the water in the amount sufficient enough to wash the target part of the body. On the other hand, the water container in an empty state can be folded into a smaller-sized shape so that it can become so compact and portable in size to be readily carried personally, for example, in a hand bag or otherwise.

In each case, when the resin film member is joined securely together with each other to form a bag-shaped container by thermally fusing or otherwise, an opening is provided at an appropriate location of the water container, e.g., at an upper edge portion thereof, without thermally fusing or otherwise. The water supply tube is attached to the water container through the opening of the water container.

As the water container is formed from the synthetic resin film member composed of the resin films cut in a shape to form a bag-shaped container and joined securely together with each other by thermally fusing or otherwise, the cut edges of the resin films may be so sharp that the hand gripping the resulting water container may be wounded. In order to prevent the hand from being wounded by the sharp edges, the front and rear wall sections may be thermally fused with a margin left non-fixed on the both sides. In a more preferred mode of this embodiment, the edge portion of the resulting water container can preferably provided with a wave-shaped fringe. With this configuration, the edge portion of the water container can be made softer than the cut and thermally fused edge portion of the water container. Further, this configuration may increase the contact area between the edge portion of the water container and the hand gripping the water container. These features can effectively prevent the hand gripping the water container from sliding along the edge portion of the water container and consequently being wounded.

It is to be noted herein, however, that the water container to be used for the present invention is not restricted to a particular one as described above in connection with the water container of the present invention and that the present invention encompasses within the scope of the invention a water container in any form appropriate for use in accordance with the present invention.

The water supply tube may be in a cylindrical form and have a water passage over the entire axial length thereof through which the water present in the water container flows from the water container by the pressure applied to the water container. The lower portion of the water supply tube is firmly fixed to the innermost surface portion of the water container by thermally fusing process or otherwise. The water supply tube may be provided with a male thread portion at its upper end so as to be engaged with the spray nozzle.

A portion of the water supply tube located inside the water container is fixed to the innermost surface portion of the water container through a plate-shaped connection that can be thermally fused or otherwise securely or integrally with the water container. The fixing of the water supply tube to the water container through the plate-shaped connection serves as a stable positioning of the water supply tube upon use. In conventional cases, the positioning of the water supply tube is unstable whenever the user grips and presses the water container to force the water out for washing the local part of the body, so that great attention has to be paid upon use in order to allow the water to be sprayed onto the target part of the body without wetting the other parts. For the portable, locally washing hygienic device according to the present invention, the position and direction of spraying the water through the spray nozzle can be made constant and stable whenever the water is forced out therefrom by gripping and pressing the water container, because the plate-shaped connection can fit the hand gripping the water container and serves as a stabilizer for positioning the water supply tube, thereby leading to the stable positioning of the spray nozzle.

Further, the water supply tube may be curved at the male thread section so as to fit the spray nozzle engaged therewith to spray the water onto the target part of the body for washing. The curved portion of the water supply tube results in the connection of the spray nozzle in a curved fashion, so that the user can direct the spray nozzle readily to the target part of the object without taking a very unnatural posture upon washing. It is to be noted herein, however, that the water supply tube is not restricted to this particular shape and form and any appropriate shape and form can be applied to the water supply tube. In some cases, it may be rather inconvenient to use the water supply tube with such a curved portion and convenient to use a generally straight water supply tube. It can be said particularly so when another person takes care of a patient or the aged who cannot use it without help by another person.

The portion of the water supply tube lower than the curved portion thereof, i.e., the top portion of the water supply tube, may be reinforced to form a reinforcement wall section. Further, the reinforcement wall section so formed can prevent a water passage hole of the water supply tube from being crushed due to the transformation of the water supply tube by the heat and pressure applied upon thermally fusing or otherwise the water supply tube with the water container. Moreover, the reinforcement wall section can serve as protecting the water passage inlet of the water supply tube from being clogged or broken upon thermally fusing or otherwise. Furthermore, a secondary flange is provided at its intermediate portion on the peripheral side of the reinforcement wall section of the water supply tube. The lower peripheral portion of the reinforcement wall section immediately adjacent the secondary flange portion serves as an attachment portion to which the top opening portion of the water container is thermally fused or otherwise, and attached in a liquid tight manner so as for the water present in the water container to fail to leak from a gap between the opening of the water container and the water supply tube upon pressing the water container by the hand.

The attachment of the water container to the water supply tube may be performed in various ways. The water supply tube may be mounted on the water container before or after the water container is formed into a bag-shaped container. For simplifying the process of production, it is preferred to attach the water supply tube on the water container before the formation into the bag-shaped container.

The water supply tube attached to the water container is then engaged with the spray nozzle.

The spray nozzle for the portable, locally washing hygienic device has a water flow passage disposed inside over its entire length and is provided with a concave portion at the bottom portion thereof. The concave portion is provided with a female thread section on the inner peripheral wall section thereof, and the spray nozzle can be engaged through the female thread section thereof with the male thread section of the water supply tube.

Upon engagement of the spray nozzle with the water supply tube, a valve assembly is disposed and fixed to the inner surface of the concave-shaped bottom portion of the spray nozzle. The structure of the valve assembly will be described in more detail hereinafter. The valve assembly allows the water present in the water container to pass through the water passage to the water passage in the spray nozzle, when the water container is gripped and pressed by the hand of the user and the water is forced out through the water supply tube from the water container, and serves as a one-way valve that can prevent the water from returning to the water container upon stopping to press the water container and supply the water from the water supply tube to the spray nozzle.

The spray nozzle includes a nozzle head mount section at the top end portion thereof, on which a nozzle head is mounted so as to be rotatable and detachable. The nozzle head is further provided with one or more water spray outlets through which the water can be sprayed through a nozzle head onto the target part of the object.

On the other hand, the nozzle head mount section is provided with an O-ring that allows the nozzle head to be attached on the spray nozzle and detached therefrom as well as to readily rotate about the nozzle head mount section.

The nozzle head in an embodiment has one water spray outlet disposed at its top end portion and communicating with the water passage of the water supply tube through the spray nozzle so as to jet and spray water onto a target part of the object in the direction extending straight through the water flow passage of the spray nozzle. On the outer periphery of the nozzle head is provided a protrusion portion which can assist in making the nozzle head easy to be mounted or detached as well as to rotate with respect to the spray nozzle. The detachable mounting of the nozzle head on the nozzle head mount section allows a provision of various types of portable, locally washing hygienic devices suitable for a variety of uses simply by changing the nozzle head. The nozzle head is suitable particularly for taking care of a patient or who needs assistance by others. It is to be noted herein, however, that the nozzle head is not restricted to such a particular type and nozzle heads can be modified so as to adapt to various uses by changing the position, size and/or number of the water jet hole and otherwise.

For example, a nozzle head in another embodiment is configured such that three water spray outlets are disposed so as to allow the water to jet in the direction normal to the direction in which the spray nozzle extends. The three water spray outlets assist in spraying water onto a wider area of the target part of the object and makes it easy to wash the target part thereof.

A nozzle head in a further embodiment is provided with one water spray outlet which can jet and spray the water in the direction at a right angle with respect to the extending direction of the spray nozzle.

The nozzle head is detachably mounted on the nozzle head mount section, so that portable, locally washing hygienic device suitable for use with various purposes can be modified with ease simply by exchanging different types of nozzle heads suitable for such various uses.

Moreover, the nozzle head may be provided with a protrusion section at the outer peripheral wall surface portion thereof, thereby enabling an easy attachment and detachment of the nozzle head to and from the nozzle head mount section and an easy rotation of the nozzle head around the spray nozzle. The rotatable mounting of the nozzle head can assist in adjusting the direction of jetting and spraying water so as to readily wash the target site of the object. The nozzle head may be particularly suitable for use in washing the anal and perianal areas of the body or for use with a bidet. It is to be noted herein, however, that the types of the nozzle head are not restricted to those as described above and they may be modified in various forms so as to adapt to various purposes of uses.

A description will now be made of the valve assembly interposed between the spray nozzle and the water supply tube. The one-way valve assembly comprises a casing with one water passage hole or more, a valve section made of an elastic material, and a pressing member disposed to press the valve section toward the casing thereonto and fixing the valve section to the inner surface of the casing.

For the valve assembly, the casing may be of a cylindrical form having a central depression with an opening or openings, which depression comprises an inner side wall section, a flange section around the upper and outer peripheral edge portion of the inner side wall section, and a bottom section disposed on the bottom end of the inner side wall section and constituting the bottom of the depression.

The flange section of the casing is configured such that the outermost peripheral diameter is substantially equal to the inner diameter of the female thread section, and that it is pressed onto the inner surface of the spray nozzle by way of the tip portion of the male thread section of the water supply tube upon engagement of the water supply tube with the spray nozzle.

In the bottom section of the casing, there may be provided a water passage hole or holes at its central portion to allow the water to pass therethrough from the water supply tube. In this embodiment, the bottom section is provided with six water passage holes, although the number of the holes is not limited to a particular one.

The valve section may be made of a synthetic rubber and the bottom surface of the valve section may assume the form of a sucker. The sucking surface area of the bottom surface can come into abutment with the top surface area of the bottom wall so as to close the water passage hole or holes due to the pressure caused by the pressing member pressing the valve section downward onto the casing.

On the other hand, the valve section may be provided on the top surface area thereof with a support protrusion so as to come into contact with the pressing member that presses the valve section onto the casing and fix it thereto.

The pressing member has a support wall section which is provided with two engagement wall sections, each has an outer peripheral surface area thereof disposed so as to come into abutment with the inner peripheral surface area of the side wall section of the casing. The bottom end of each of the engagement wall sections of the pressing member is allowed to come into contact with the upper peripheral edge portion of the valve section in order to press the valve section onto the casing and fix the former to the latter.

The support wall section is provided with a water passage hole or holes so as to allow the water to flow into the hole or holes through the valve section, more specifically, through a gap around the peripheral edge portion of the valve section, from the casing. More specifically, when the water container is pressed by the hand and the water is forced out from the water container through the water supply tube, the water passes through the water passage hole or holes of the casing and pushes off the valve section to open a gap between the inner surface of the casing and the peripheral edge portion of the valve section and to allow the water to pass through the gap, and the water passing through the valve section is allowed to flow through the water passage hole or holes of the pressing member.

Upon actual use of the portable, locally washing hygienic device, the spray nozzle is detached from the water supply tube and water is supplied to the respective water containers from a top opening of the water supply tube. As the water container has been filled with the water to an appropriate level, the water supply tube is engaged with the spray nozzle with the valve assembly disposed within the female thread section, and then the portable hygienic device is ready for use.

As the water container is gripped and pressed by the hand, a pressure is applied to the water present in the water container, and the water is forced to flow through the water passage of the water supply tube, followed by reaching the valve assembly. Then, the water flown in the casing of the valve assembly transforms the valve section of the valve assembly to open a gap between the valve section and the bottom section of the casing. In other words, the water entering in the casing pushes the valve section upward to open a gap at the periphery of the valve section to allow the water to flow through the gap. As a result, the water present in the water container is forced out through the gap toward the spray nozzle and eventually jetted and sprayed from the nozzle head onto the target part of the body and wash it.

On the other hand, as the force of gripping the water container is loosened, the transformation of the valve section is recovered to its original state, and the valve section is allowed to tightly attach again to the inner surface of the bottom section of the casing and close the water passage hole or holes of the casing, thereby eventually preventing the water from returning back from the nozzle head to the water container.

The portable, locally washing hygienic device according to the present invention can offer the advantages in that as the plate-shaped connection of the water supply tube is thermally fused or otherwise with the inner surface portion of the front wall section of the water container, the direction of the spray nozzle with respect to the water supply tube does not change to a great extent even if the water container is gripped and pressed by the hand. Therefore, the direction in which the water is jetted and sprayed from the nozzle head can be kept in a substantially constant fashion, so that the target part of the body can be washed with ease.

Moreover, the portable hygienic device according to the present invention can be used continually for jetting and spraying the water without sucking air into the water container, so that the mechanism of the portable hygienic device, particularly the valve mechanism, can be simplified. As a result, the portable hygienic device according to the present invention can be prepared at low costs.

In addition, no metal part is used for the valve assembly and any other part of the portable, locally washing hygienic device. Therefore, the portable, locally washing hygienic device can be disposed of easily because no work is required for separation of such metal parts from the portable hygienic devices upon disposal.

It is to be understood herein that the water container according to the present invention is not restricted to the specific modes of the water containers as described above and the present invention encompasses within the scope and spirit of the invention any modifications and variations of the water containers without departing the scope and spirit of the present invention.

Then, a description will be made of a specific construction of the portable, locally washing hygienic device according to the present invention with reference to the accompanying drawings.

Figure 2:
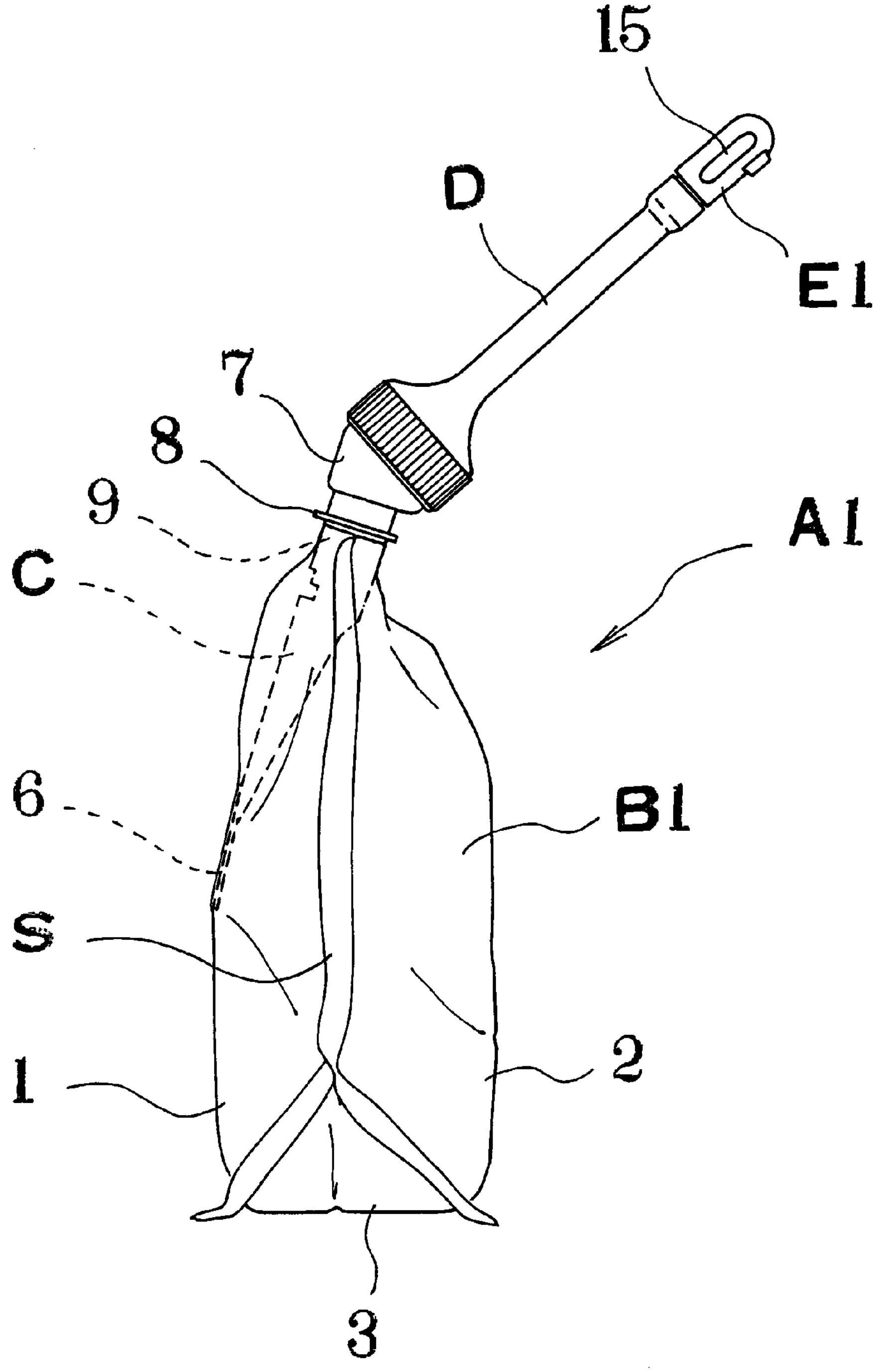
FIG. 2 is a side view showing the portable, locally washing hygienic device according to the first embodiment of the present invention.

Referring to FIGS. 1 and 2, the portable, locally washing hygienic device A1 in a first embodiment of the present invention is shown which comprises a water container B1, a water supply tube C engaged with the water container B1, a spray nozzle D mounted on the water supply tube C, and a valve assembly F interposed between the water supply tube C and the spray nozzle D.

The water container A1 may be made of a synthetic resin film member which is prepared, for example, by laminating a thermally fusable resin film of a polyethylene type or a polypropylene type with a substrate such as, for example, a synthetic resin film, paper, aluminum foil or the like. The water container A1 may be formed in such a manner that the thermally fusable resin film of a polyethylene type or a polypropylene type is disposed as an innermost surface portion of the resulting water container. It is to be noted herein that the material for the synthetic resin film member is not restricted to such a particular one and any material can be used as long as it can attain the purposes of the present invention.

The water container B1 may be prepared by laminating the synthetic resin film for the outer portion of the water container on the synthetic resin film for the innermost surface portion thereof and thermally fusing or otherwise the edge portions of the synthetic resins in conventional manner into the form of a bag-shaped container.

As shown in FIGS. 1 and 2, the water container B1 comprises a front wall section 1, a rear wall section 2, and a bottom section 3 and may be formed into a bag-shaped form by joining top and side edge portions of the front and rear wall sections 1 and 2 securely together, with a part of the top edge portion left non-joined to form an opening, and by joining bottom edge portions of the front and rear wall sections 1 and 2 securely together with all the edge portions of the bottom section 3. The secure joining of the front wall, rear wall and bottom sections 1, 2 and 3, respectively, can provide a bag-shaped container B1 in which water can be filled, and the resulting bag-shaped container B1 has an opening at the top portion through which it is connected with the spray nozzle D. This construction allows the bottom portion of the water container B1 to expand over the entire width of the bottom section 3 into a generally triangular form, as viewed from the side, and into a generally oval form, as viewed from bottom, when the water container is filled with water.

Figure 3:
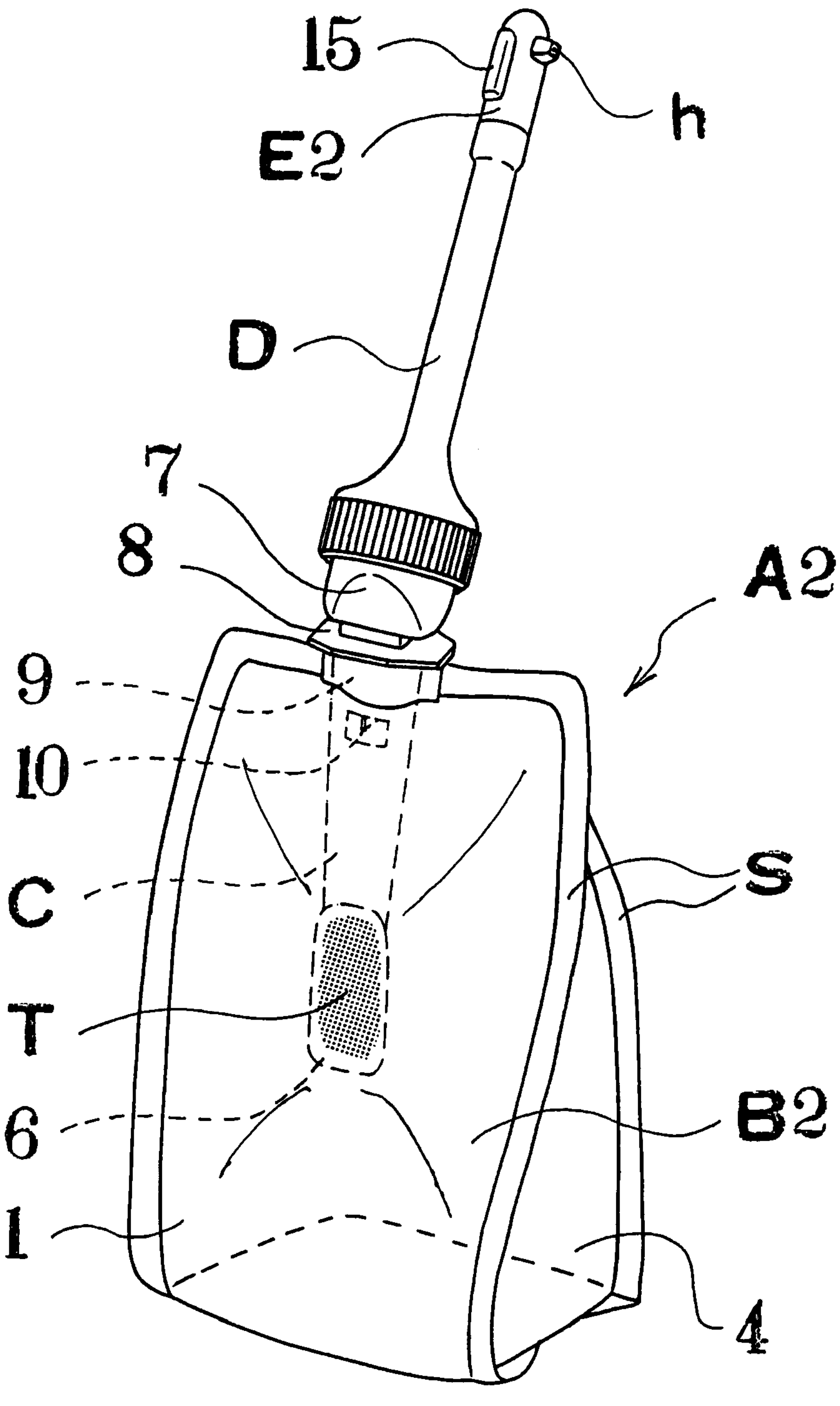
FIG. 3 is a perspective view showing a portable, locally washing hygienic device according to a second embodiment of the present invention.

Alternatively, FIG. 3 shows a water container B2 according to a second embodiment of the present invention, which comprises a front wall section 1, a rear wall section 2, and a pair of side wall sections 4. The water container B2 may be formed into a bag-shaped container by joining top and bottom edge portions of the front and rear wall sections 1 and 2, respectively, with each other securely together, with a part of the top edge portion left non-joined to form an opening, and joining the side edge portions of the front and rear wall sections 1 and 2, respectively, with all the side edge portions of the pair of the side wall sections 4 securely together. This construction can provide a bag-shaped container B2 in which water can be filled, like the water container B1, and the resulting bag-shaped container B2 has an opening at the top portion through which it is connected with the spray nozzle D. This construction of the water container allows the side portion of the water container B2 to expand over the entire width of the side wall sections into a generally oval form, as viewed from the side, when the water container is filled with water.

For each of the water containers B1 and B2, the joining of the front, rear and side wall sections or the front wall, rear wall and bottom sections may be carried out in conventional manner, including, for example, thermally fusing or otherwise. A joined edge portion is referred to herein as reference symbol "S".

Figure 4:
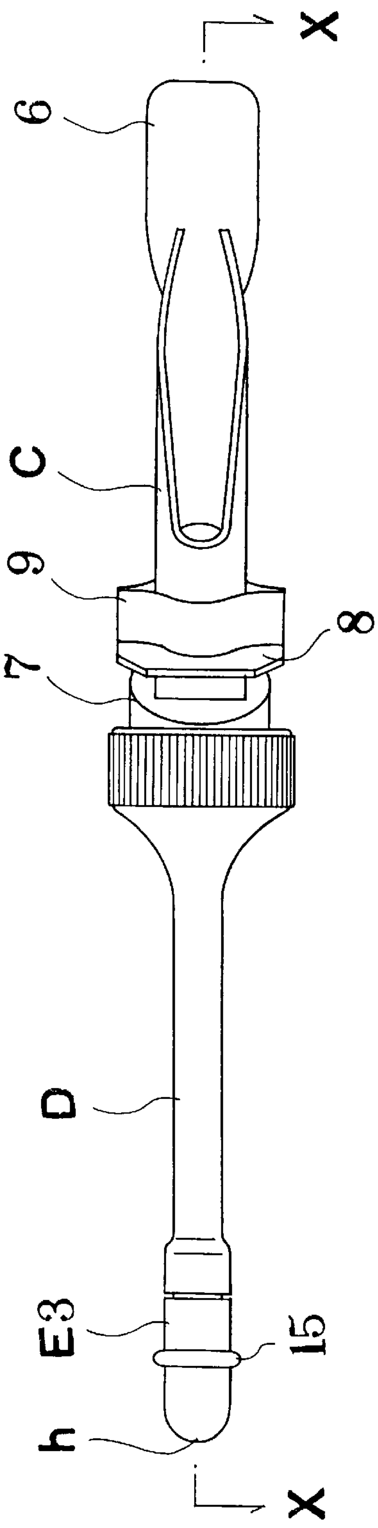
FIG. 4 is a plan view showing a spray structuring portion for spraying water.
Figure 5:
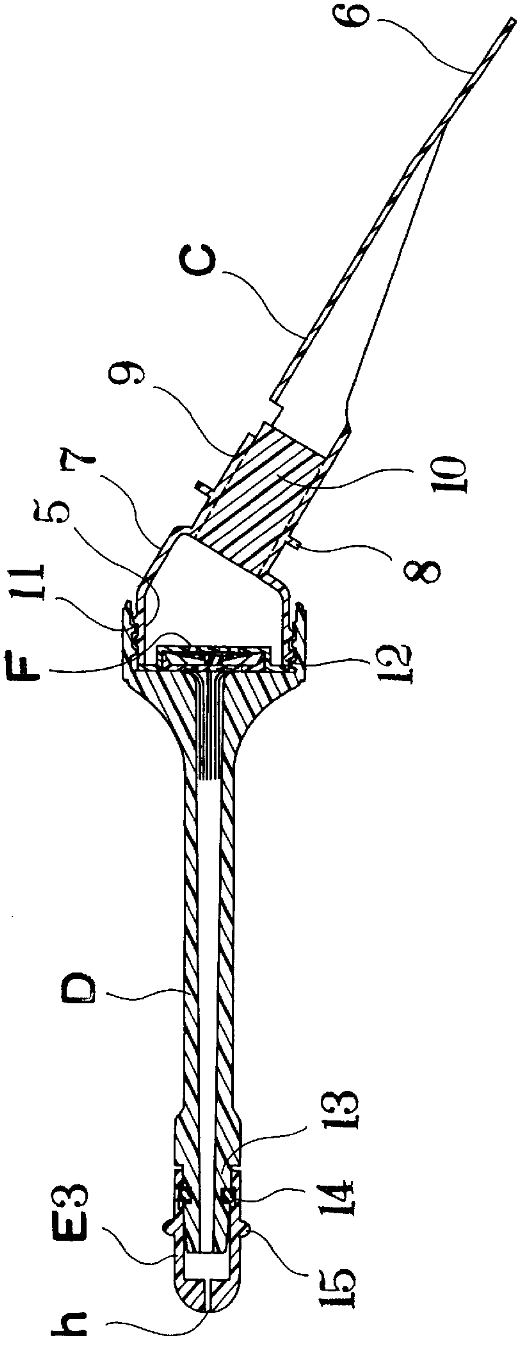
FIG. 5 is a sectional view showing the spray structuring portion, when taken along line X—X of FIG. 4.

As shown in FIGS. 4 and 5, the water supply tube C is provided with a plate-shaped connection 6 at its lower portion. The water supply tube C is further provided with a water passage opening on the opposite side of the plate-shaped connection 6, through which water can flow from the water container and be forced out into the spray nozzle D by pressing the water container strongly by the hand of a user. Further, the plate-shaped connection 6 may be thermally fused or otherwise with and attached to the innermost surface layer of the front wall section 1 of the water container. It is to be noted herein, however, that the portion to which the plate-shaped connection 6 is attached together is not limited to the inner surface portion of the front wall section 1 of the water container, as shown in FIGS. 1 to 3, and it may be attached together to the innermost surface layer of the rear wall section 2. It is also to be noted that the lower portion of the water supply tube can be joined securely together with the innermost surface portion of the water container by any appropriate process equivalent to the thermally fusing process. The hatched portion as shown in FIG. 1 indicates a thermally fused portion T of the plate-shaped connection 6.

As specifically shown in FIG. 5, the water supply tube C is curved at the upper portion thereof, and the male thread section 5 may be formed on the curved portion 7 so as to be engaged with the spray nozzle D. Therefore, the spray nozzle D can be connected to the water supply tube C in a curved fashion, thereby making it likely to fit the direction of spraying the water from the spray nozzle to the target part of the object.

A portion of the water container lower than the curved portion 7 includes a reinforcement wall section 10 that can serve as preventing a water passage hole of the water supply tube C from being broken due to the transformation of the water supply tube C by the heat and pressure applied upon thermally fusing or otherwise the water supply tube C with the water container. The reinforcement wall section 10 may be provided at an outer periphery thereof with a secondary flange 8 that may serve as the uppermost boundary of the binding between the water container and the water supply tube C. A peripheral side portion of the water supply tube C lower than the secondary flange 8 is referred to herein as a binding portion 9 on which the water container is joined securely together with the water supply tube C. The joining of the water supply tube C with the water container may be conducted by inserting the water supply tube C into the water container through the opening at the top edge portion of the water container and joining the opening of the water container with the binding portion 9 of the spray nozzle D securely together, for example, by thermally fusing or otherwise.

The spray nozzle D for the portable hygienic device has a water flow passage disposed inside over its entire length, the water flow passage being disposed and extending so as to communicate with the water passage in the water supply tube C and flow the water stream through the water passage opening of the water supply tube C from the water container and to spray the water through the spray nozzle D, as specifically shown in FIG. 5.

The spray nozzle D includes a concave-shaped bottom section that is further provided with a female thread section 11 on the inner peripheral wall portion thereof, which can be engaged with the male thread section 5 of the water supply tube C, as shown in FIG. 5. It is to be noted herein that the inner peripheral side wall portion of the concave-shaped bottom section may be provided with a male thread section, in place of the female thread section, if convenient, however, in this case, as a matter of course, a female thread section, in spite of the male thread section, may be provided on the water supply tube C.

Figure 6:
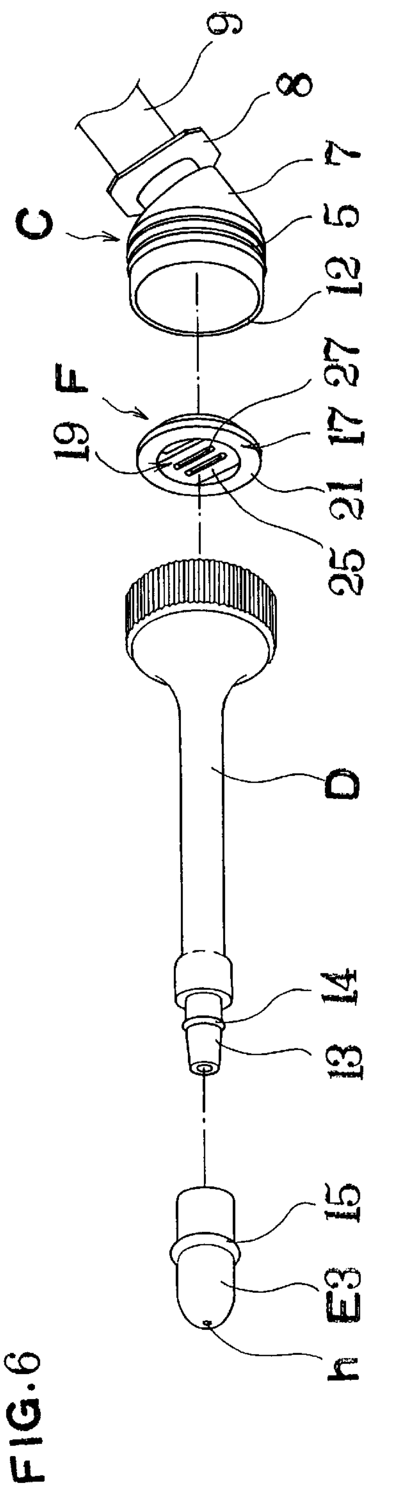
FIG. 6 is an exploded view of the spray structuring portion.

Moreover, the valve assembly F is disposed in the concave-shaped bottom section and fixed to the inner surface at the bottom of the spray nozzle D by pressing the valve assembly F by way of a tip portion 12 of the male thread section 5 of the water supply tube C and fixed by engagement of the spray nozzle D with the water supply tube C, as shown in FIGS. 5 and 6.

On the other hand, as shown in FIGS. 5 and 6, the top end portion of the spray nozzle D forms a nozzle head mount section 13, and the nozzle head mount section 13 in turn is provided with an O-ring 14 that allows the nozzle head E3 to be attached on the spray nozzle D and detached therefrom as well as to readily rotate about the nozzle head mount section 13.

As shown in FIGS. 4 to 6, the nozzle head E3 has one water jet hole h disposed at its top end portion so as to jet water onto a target site of the object in the direction extending straight through the water flow passage of the spray nozzle D. On the outer periphery of the nozzle head E3 is provided a protrusion portion 15 which can assist in making the nozzle head E3 easy to be mounted or detached as well as to rotate with respect to the spray nozzle D. The detachable mounting of the nozzle head E3 on the nozzle head mount section 13 allows a provision of various types of portable, locally washing hygienic devices suitable for a variety of uses simply by changing the nozzle head E3. The nozzle head E3 as shown in FIGS. 4 to 6 is suitable particularly for taking care of a patient or who needs assistance by others. It is to be noted herein, however, that the nozzle head is not restricted to such a particular type and nozzle heads can be modified so as to adapt to various uses by changing the position, size and/or number of the water jet hole h and otherwise.

For example, as shown in FIGS. 1 and 2, a nozzle head E1 is configured such that three water jet holes h are disposed so as to allow the water to jet in the direction normal to the direction in which the spray nozzle D extends. The three water jet holes h assist in spraying water onto a wider area of the desired object and makes it easy to wash the target part of the object.

As shown in FIG. 3, a nozzle head E2 is provided with one water jet hole h having an inner diameter than the water jet hole h of the nozzle head E1, which can jet the water in the direction at a right angle with respect to the extending direction of the spray nozzle.

Like the nozzle head E3, each of the nozzle heads E1 and E2 is detachably mounted on the nozzle head mount section 13, so that portable, locally washing hygienic devices suitable for use with various purposes can be modified with ease simply by exchanging different types of nozzle heads for each of the spray nozzles E1 and E2.

Moreover, likewise in the case of the nozzle head E3, each of the nozzle heads E1 and E2 may be provided with a protrusion section 15 at the outer peripheral wall surface portion thereof, thereby enabling an easy attachment and detachment of the nozzle head to and from the nozzle head mount section 13 and an easy rotation of the nozzle head around the spray nozzle. The rotatable mounting of each of the nozzle heads E1 and E2 can serve as adjusting the direction of jetting water so as to readily wash the target site of the object. The nozzle head E1 is particularly suitable for use in washing the anal and perianal areas of the body, and the nozzle head E2 is particularly for use with a bidet. It is to be noted herein, however, that the above-mentioned types of the nozzle heads are not restricted to those as described above and they may be modified in various forms so as to adapt to various purposes of uses.

Now, a description will be made of the valve assembly F with reference to the accompanying drawings.

Figure 8:
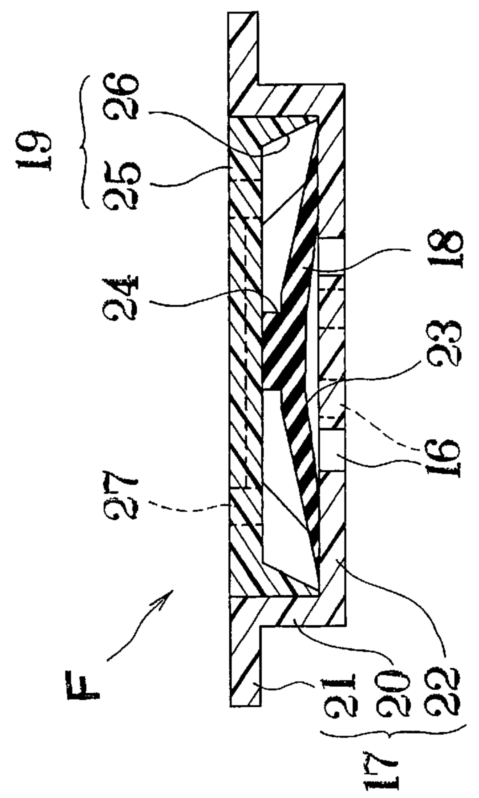
FIG. 8 is a sectional view of the valve section.
Figure 7:
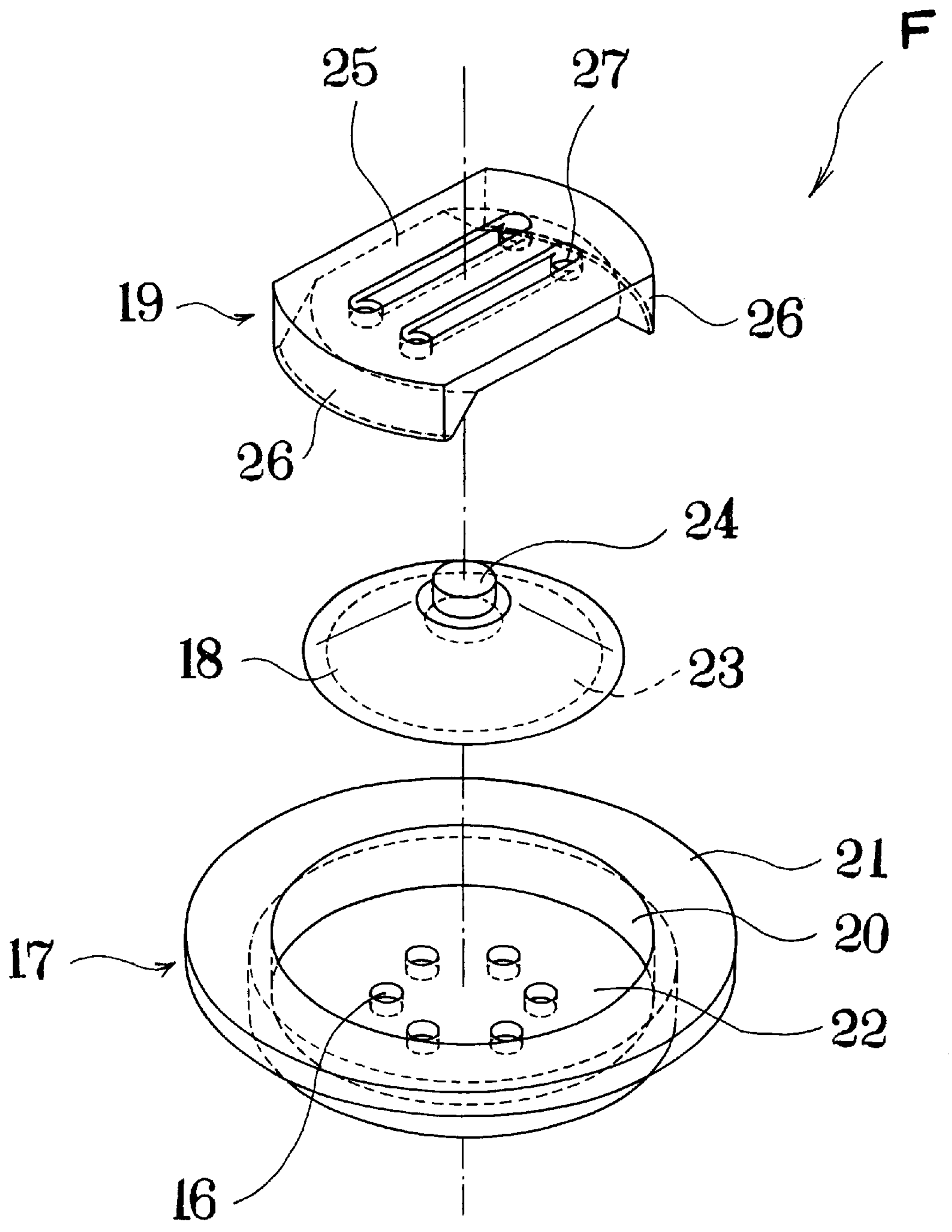
FIG. 7 is an exploded view of the valve section.

As shown in FIGS. 7 and 8, the valve assembly F interposed between the spray nozzle D and the water supply tube C comprises a casing 17 with water passage hole or holes, referred to generally as 16, a valve section 18 made of an elastic material, and a pressing member 19 disposed to press the valve section 18 toward the casing 17 thereonto and fixing the valve section 18 to the inner surface of the casing 17. Further, the valve assembly F is firmly fixed to the spray nozzle D by the aid of the tip portion 12 of the water supply tube C, while the water supply tube C is tightly engaged with the spray nozzle D through their thread sections, thereby tightly fixing the valve assembly to both of the water supply tube C and the spray nozzle D.

For the valve assembly F, the casing 17 may be of a cylindrical form having a central depression with an opening or openings, which depression comprises an inner side wall section 20, a flange section 21 around the upper and outer peripheral edge portion of the inner side wall 20, and a bottom section 22 disposed on the bottom end of the inner side wall section 20 and constituting the bottom of the depression.

The flange section 21 of the casing 17 is configured such that the outermost peripheral diameter is substantially equal to the inner diameter of the female thread section 5, and that it is pressed onto the inner surface of the spray nozzle D by way of the tip portion 12 of the male thread section 11 of the water supply tube C upon engagement of the water supply tube C with the spray nozzle D.

In the bottom section 22 of the casing 17, there is or are provided a water passage hole or holes 16 to allow the water to pass therethrough. In this embodiment, the bottom section 22 is provided with six water passage holes 16 and the diameter of each hole is set to be about 1 mm although the size of each hole 16 is not limited to a particular one.

The valve section 18 is made of a synthetic rubber and the bottom surface 23 assumes the form of a sucker. The sucking surface area of the bottom surface 23 can come into abutment with the top surface area of the bottom wall 22 so as to close the water passage hole or holes 16 due to the force of the pressing member 19 pressing the valve section 18 onto the casing 17.

On the other hand, the valve section 18 may be provided on the top surface area thereof with a support protrusion 24 so as to come into contact with the pressing member 19 that presses the valve section 18 onto the casing 17 and fix it thereto.

The pressing member 19 has a support wall section 25 which is provided with two engagement wall sections 26 and 26, each has an outer peripheral surface area thereof disposed so as to come into abutment with the inner peripheral surface area of the side wall section 20 of the casing 17. The bottom end of each of the engagement wall sections 26 and 26 of the pressing member 19 is allowed to come into contact with the upper peripheral edge portion of the valve section 18 in order to press the valve section 18 onto the casing 17 and fix the former to the latter.

The support wall section 25 is provided with a water passage hole or holes 27 so as to allow the water to flow into the hole or holes 27 through the valve section 18, specifically, through a gap around the peripheral edge portion of the valve section 18, from the casing 17. More specifically, the water passing through the water passage hole or holes 16 of the casing 17 flows in the space between the water supply tube C and the spray nozzle D and pushes off the valve section 18 to open a gap between the inner surface 22 of the casing 17 and the peripheral edge portion of the valve section 18 and to allow the water to pass through the gap, and the water passing through the valve section 18 is allowed to flow through the water passage hole or holes 27 and reach the nozzle head portion without staying in the spray nozzle D.

Upon actual use of the portable, locally washing hygienic device according to the present invention, the spray nozzle D is detached from the water supply tube C and water is supplied to the water container from the top end portion 12 of the water supply tube C. As the water container has been filled with the water to an appropriate level, the water supply tube C is engaged with the spray nozzle D with the valve assembly F interposed between the water supply tube C and the spray nozzle D, and then the portable hygienic device is ready for use.

Figure 9:
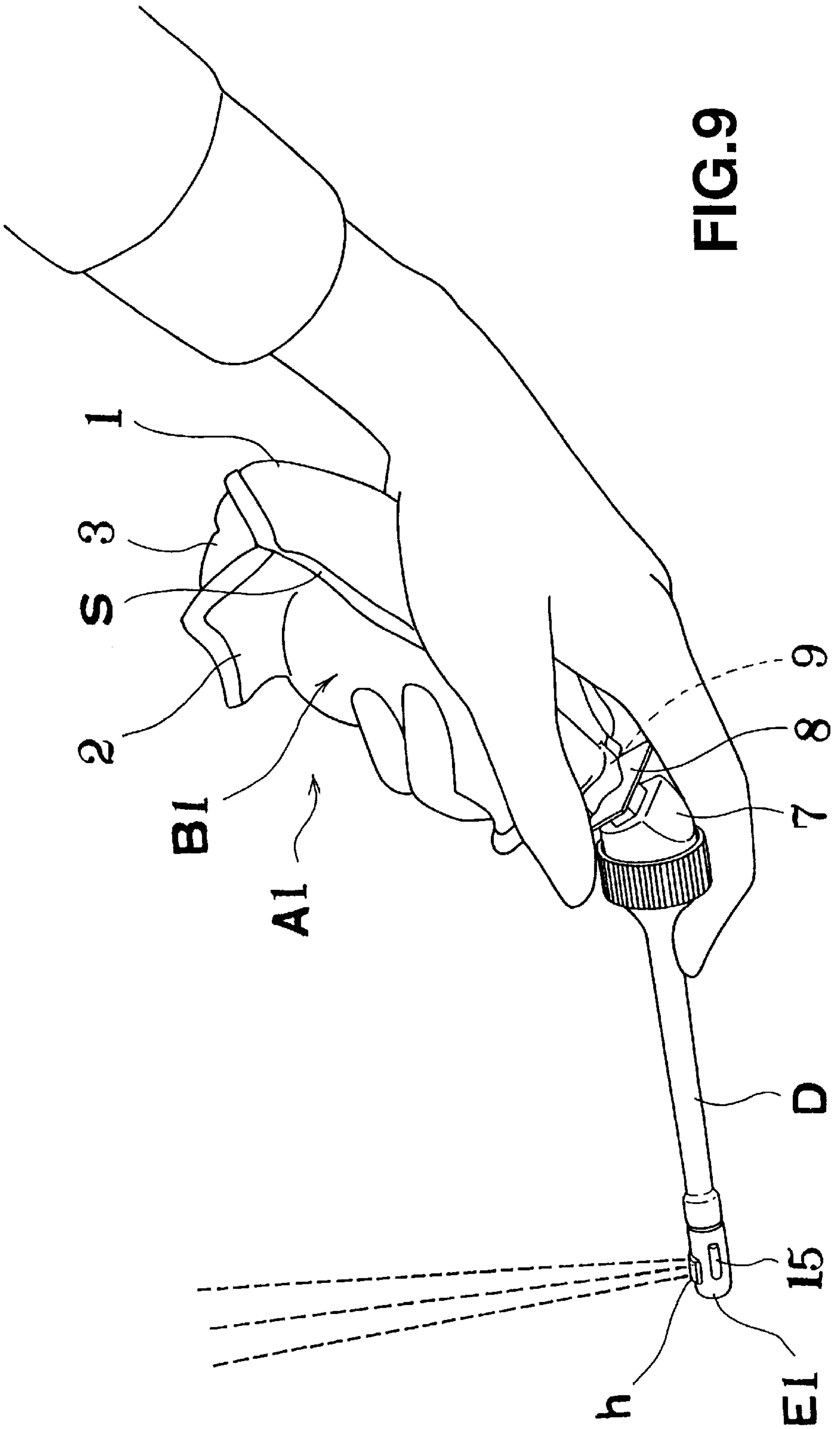
FIG. 9 is a schematic view showing the state of use of the portable, locally washing hygienic device according to the first embodiment of the present invention.

As shown in FIG. 9, as the water container is gripped by the hand, a pressure is applied to the water present in the water container, and the valve section 18 of the valve assembly F is transformed to open a gap between the valve section 18 and the bottom section 22 of the casing 17. As a result, the water present in the water container is forced out through the gap toward the spray nozzle D and eventually jetted and sprayed from the nozzle head onto the target part of the body.

On the other hand, as the force of gripping the water container is loosened, the transformation of the valve section 18 is recovered to its original state, and the valve section 18 is allowed to tightly attach again to the inner surface of the bottom section of the casing 17 and close the water passage hole or holes 16 of the casing 17, thereby eventually preventing the water from leakage from each of the nozzle heads and the water left in the spray nozzle from returning to the water container.

The portable, locally washing hygienic device according to the present invention can offer the advantages in that as the plate-shaped connection 6 of the water supply tube C is thermally fused or otherwise with the inner surface portion of the front wall section 1 of the water container, the direction of the spray nozzle D with respect to the water supply tube C does not deviate from its initial position to a great extent even if the water container is gripped and pressed by the hand. Therefore, the direction in spraying the water from the nozzle head can be kept in a constant fashion, so that the target part of the body can be washed with ease.

It is to be understood herein that the water container according to the present invention is not restricted to the specific modes of the water containers as described above and the present invention encompasses within the scope and spirit of the invention any modifications and variations of the water containers without departing the scope and spirit of the present invention.

A description will be made of modifications of the water container according to the present invention with reference to FIGS. 10(*a*) and 10(*b*).

Figure 10A:
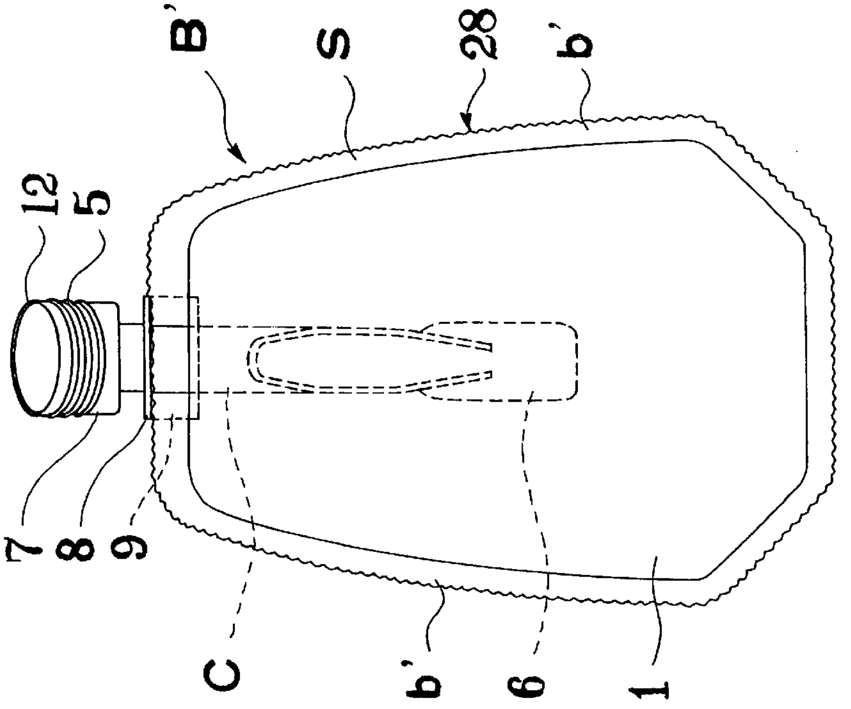
FIG. 10 is a schematic view showing a wave-shaped fringe formed at the edge portion of the water container.
Figure 10B:
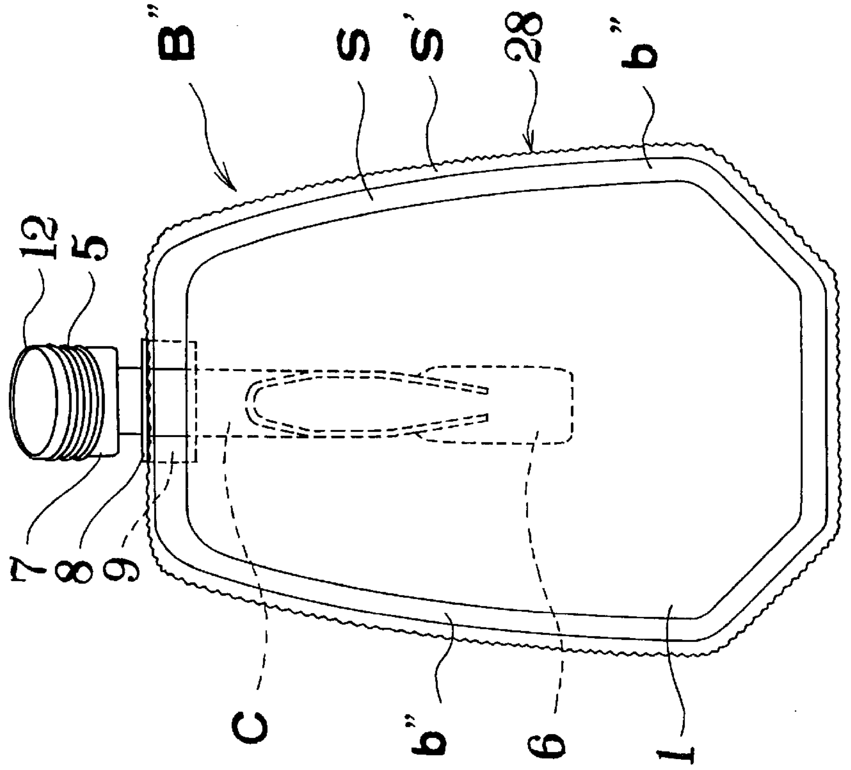

FIG. 10(*a*) shows another mode of this embodiment according to the present invention, in which the water container is made of a synthetic resin film member having a high rigidity. The water bag B' is provided with a wave-shaped fringe 28 at the outer peripheral edge of the thermally fused portion S thereof. The thermally fused portion S of the water container portion B' makes it to sharpen the side edge portion as a result of cutting process and joining together the such cut edge portions of the resin films into a bag so that the sharp edge may cause the danger that the finger may be injured upon treating the portable hygienic device. The wave-shaped fringe 28 can make the edge of the thermally fused portion S blunt and readily flexible and increase the contact area of the thermally fused portion S with the hand, so that it can prevent the hand from sliding along the edge of the water container portion B' and as a consequence reduce the risk of injuring the hand.

FIG. 10(*b*) shows a further mode of this embodiment according to the present invention, in which the water bag B" is configured such that the outer edge portion is thermally fused at the thermally fused portion S with an outermost edge portion S' left non-fixed thermally. The thermally non-fixed edge portion S' is disposed to enclose the thermally fused portion S and is not caused to cure so that the edge of the non-fixed edge portion S' is not so sharp and is soft and flexible to cause no risk of cutting the hand as the bag B" is gripped and pressed by the hand. Further, the non-fixed edge portion S' may be fringed with a wave-shaped edge as in the mode shown in FIG. 10(*a*).

It is to be noted herein that the shape of the fringe 28 at the side edge of the thermally fused portion S or the non-fixed portion S' is not restricted to the wave-shaped form as described above in connection with the above embodiments and may be in any form, such as in a mountain-and-valley form or a cycloid form, as long as it can achieve the effects as sought to be gained by the provision of the modified fringe 28. It was found as an experiment on various shapes of the fringe, however, that a wave-shaped fringe each having a 2 mm pitch can fit the hand as the bag is gripped by the hand and it can be handled easily.

As shown in FIGS. 10(*a*) and 10(*b*), the thermally fused portion S on each of the both sides b' and b" of the water containers B' and B", respectively, may be formed such that the middle section of the fused portion S is curved outwardly in a convex shape. This form of the thermally fused portion S of each of the water container B' and B" can assist in making the fused portion S readily flexible so that the water container B' and B" can fit the hand easily.

EFFECTS OF THE INVENTION

The portable, locally washing hygienic device according to the present invention includes the water container made of a flexible bag-shaped container formed by the synthetic resin film member, the water supply tube mounted on the water container and acting as a water passage from the water container, the spray nozzle mounted on the top end portion of the water supply tube, and the valve assembly interposed between the water supply tube and the spray nozzle. This construction of the portable, locally washing hygienic device can make the total weight of the portable hygienic device light so as to be carried readily because the portable, locally washing hygienic device can be folded in a small and compact size. Further, the water supply tube is joined at its lower portion inside the water container together with the innermost surface portion of the water container, so that the portable, locally washing hygienic device ensures a substantially constant direction of spraying water therefrom without paying great attention to the direction of spraying the water toward the target part of the object and locally washing the target part thereof, whenever the user presses the water container for forcing the water out therefrom to spray it onto the target portion of the object for washing.

In a preferred mode of the present invention, the joining of the water supply tube with the water container through the plate-shaped connection can effectively prevent the water supply tube from being removed from the innermost surface portion of the water container, thereby ensuring a stable handling of the portable hygienic device.

In another preferred mode of the present invention, the valve assembly acting as a one-way valve is interposed between the water supply tube and the spray nozzle. A further preferred mode of this embodiment resides in that the one-way valve comprises the casing with the water passage hole formed therein, the valve section made of an elastic material, and the pressing member for pressing the valve section toward the casing so as to fail to cause the water to flow through a water passage in the water supply tube from the water container to the spray nozzle in usual cases, i.e., without pressing the water container. This construction enables the user to readily adjust the magnitude of the pressure for spraying the water onto the target part of the object and thoroughly prevent a leakage of the water from the portable hygienic device upon use or while being carried with water filled therein. Further, no metal parts are used for the opening-closing mechanism including the valve assembly, so that no laborious work for removing metal parts from the portable hygienic device is required, thereby shortening the disposal work time and enabling a ready disposal of the portable hygienic device when it is not used any more.

Moreover, the portable hygienic device according to the present invention does not require any air supply whenever water is forced out from the water container, so that a necessary amount of the water can be sprayed onto the target part of the object simply by gripping the water container and pressing it by the hand. Therefore, the portable hygienic device can be provided with a simple valve mechanism for spraying water, so that it can be prepared at low costs of production.

In a further preferred mode of the present invention, the water supply tube is provided at its upper end portion with the curved section so that the spray nozzle is connected to the water supply tube, i.e., the water container, in a curved fashion so as to fit the nozzle head of the spray nozzle to spray the water onto and wash the target part of the body in a natural and comfortable posture without taking an unnatural posture upon use.

In a still further preferred mode of the present invention, the spray nozzle head is detachably mounted on the top end portion of the spray nozzle. Therefore, the portable, locally washing hygienic device can be provided for versatile uses at low costs of production simply by exchanging nozzle heads suitable for intended use.

Further, in a still further preferred mode of this embodiment of the present invention, the nozzle head can be rotatably mounted on the top portion of the spray nozzle, so that the direction of spraying the water from the nozzle head can be adjusted readily and the portable hygienic device can be applied in a natural and comfortable posture.

Moreover, in another preferred mode of the present invention, the water container is formed into a bag-shaped container by joining the edge portions of synthetic resin films, e.g., by thermally fusing or otherwise. The side edge of the joined edge portions of the water container is provided with a wave-shaped fringe, so that the contact area between the hand gripping and pressing the water container and the side edge can be increased, thereby preventing the hand from sliding along the side edge of the water container and from being wounded. In a further preferred mode of this embodiment, the edge portions of the resin films are joined securely together with each other, e.g., by thermally fusing or otherwise, with a margin outside the joined edge portions left non-joined. The side edge of the non-joined edge portions of the water container is provided with a wave-shaped fringe, so that the contact area between the hand gripping the water container and the side edge can be increased, thereby preventing the hand from sliding along the side edge of the water container and from being wounded. In this case, the non-joined margin itself is softer than the joined edge portions so that it can also achieve the effect similar to the effect to be achieved by the water container with the wave-shaped fringe at its edge.

What is claimed is:

1. A portable, locally washing hygienic device, comprising:

a water container of a flexible synthetic resin film member having an opening on a top thereof; and a combination including a water supply tube, a spray nozzle section and a valve assembly, said combination being mounted in the opening of said water container;

said water supply tube having an opening formed on one side thereof and a connecting portion at another, lower side thereof, washing water received within said water container being forced into said spray nozzle section through said opening of said water supply tube upon pressing said water container, said water supply tube being connected to an inner side wall surface portion of said water container via said connection portion;

said spray nozzle section being mounted on an upper portion of said water supply tube and being located outside of said water container, washing water being sprayed through said spray nozzle section onto a target part of an object to be washed;

said valve assembly being interposed between said spray nozzle section and said water supply tube, through which washing water transferred from said water container via said water supply tube is forced into said spray nozzle section;

the connecting portion of said water supply tube being located within said water container and joined securely together with an inner surface portion of said water container, said connecting portion extending over at least a portion of a region of said water container to be gripped by a hand of a user, and pressed thereby to force the washing water onto the target part to be washed.

2. The portable, locally washing hygienic device, as claimed in claim 1, wherein said connecting portion comprises a plate-shaped connection thermally fusible with said inner surface portion of said water container.

3. The portable, locally washing hygienic device as claimed in claim 1 or 2, wherein said valve assembly comprises a one-way valve assembly configured to allow the washing water to flow from said water supply tube into said spray nozzle section upon pressing said water container, and to terminate flow from said water supply tube into said spray nozzle section and prevent back-flow from said spray nozzle section into said water supply tube upon releasing a force pressing said water container.

4. The portable, locally washing hygienic device as claimed in claim 3, wherein said one-way valve assembly comprises a casing with a water passage hole, a valve section made of an elastic material, and a pressing member pressing said valve section onto said casing so as to inhibit water from passing from said water container through said water supply tube into said spray nozzle section without pressing said water container.

5. The portable, locally washing hygienic device as claimed in claim 1 or 2, wherein said water supply tube is provided at an upper portion with a curved section through which said water supply tube in turn is connected to said spray nozzle section.

6. The portable, locally washing hygienic device as claimed in claim 1 or 2, further comprising a nozzle head detachably received at a top end portion of said spray nozzle section through which water is sprayed onto the target part of the object.

7. The portable, locally washing hygienic device as claimed in claim 6, wherein said nozzle head is rotatably mounted on said spray nozzle section.

8. The portable, locally washing hygienic device as claimed in claim 6, wherein said nozzle head has a spray outlet for spraying water in a direction in which said spray nozzle extends.

9. The portable, locally washing hygienic device as claimed in claim 8, wherein said nozzle head includes at least one spray outlet.

10. The portable, locally washing hygienic device as claimed in claim 6, wherein said nozzle head has a spray outlet for spraying water in one of a direction generally orthogonal and perpendicular to the direction in which said spray nozzle extends.

11. The portable, locally washing hygienic device as claimed in claim 1 or 2, wherein an outer edge of said water container includes a wave-shaped fringe.

12. The portable, locally washing hygienic device, as claimed in claim 11, wherein said connecting portion comprises a plate-shaped connection thermally fusible with said inner surface portion of said water container.

13. A portable, locally washing hygienic device, comprising:

a water container of a flexible synthetic resin film member including a joined edge portion, an outer edge portion of said water container outside said joined edge portion thereof remains non-joined;

a connecting member;

a water supply tube mounted on said water container and acting as a water passage, a lower portion of said water supply tube being located within said water container and joined securely together with an inner surface portion of said water container through said connecting member;

a spray nozzle mounted on an upper portion of said water supply tube; and a valve assembly interposed between said spray nozzle and said water supply tube.

14. The portable, locally washing hygienic device, as claimed in claim 13, wherein said connecting member comprises a plate-shaped connection thermally fusible with said inner surface portion of said water container.

15. The portable, locally washing hygienic device, as claimed in claim 13, wherein said non-joined outer edge portion thereof is provided with a wave-shaped fringe.

* * * * *